(12) United States Patent
Norman et al.

(10) Patent No.: US 10,869,731 B2
(45) Date of Patent: Dec. 22, 2020

(54) DISPOSABLE CONTAINER FOR MOBILE MEDICAL CART

(71) Applicant: Neonatal Product Group, Inc., Stillwell, KS (US)

(72) Inventors: Scott Norman, Stillwell, KS (US); Mark Petheram, Olathe, KS (US); Heather Fibuch-Townsend, Leawood, KS (US); Anthony Hash, Olathe, KS (US)

(73) Assignee: Neonatal Product Group, Inc., Stillwell, KS (US)

( * ) Notice: Subject to any disclaimer, the term of this patent is extended or adjusted under 35 U.S.C. 154(b) by 0 days.

(21) Appl. No.: 16/718,871

(22) Filed: Dec. 18, 2019

(65) Prior Publication Data

US 2020/0121409 A1    Apr. 23, 2020

Related U.S. Application Data

(63) Continuation of application No. 16/194,604, filed on Nov. 19, 2018, which is a continuation-in-part of
(Continued)

(51) Int. Cl.
*A61B 50/13* (2016.01)
*A61B 50/10* (2016.01)
(Continued)

(52) U.S. Cl.
CPC .............. *A61B 50/13* (2016.02); *A47B 31/02* (2013.01); *A47B 67/04* (2013.01); *A47B 81/00* (2013.01); *A47B 96/18* (2013.01); *A47B 96/201* (2013.01); *A61B 50/33* (2016.02); *A61B 50/36* (2016.02); *A61B 90/35* (2016.02); *A61G 12/001* (2013.01); *A61M 5/1417* (2013.01); *G01G 17/00* (2013.01); *G01G 19/42* (2013.01); *A47B 2031/003* (2013.01); *A47B 2031/006* (2013.01);
(Continued)

(58) Field of Classification Search
CPC ......... A61B 50/13; A61B 50/36; A61B 90/35; A47B 31/02; A47B 81/00; A47B 96/18; A47B 96/201; A61G 12/001
USPC ...... 220/62.21, 495.01, 495.08, 495.06, 662, 220/731; 312/209, 249.8, 249.11
See application file for complete search history.

(56) References Cited

U.S. PATENT DOCUMENTS 3,853,329 A * 12/1974 McDonald ........... A61G 12/001
                                                    280/47.35
8,075,071 B1 * 12/2011 Whittall ............... A47B 23/043
                                                    312/209
(Continued)

*Primary Examiner* — J. Gregory Pickett
*Assistant Examiner* — Niki M Eloshway
(74) *Attorney, Agent, or Firm* — Hovey Williams LLP

(57) ABSTRACT

A medical cart having a chassis with a plurality of wheels attached thereto; a plurality of drawers supported on the chassis; a temperature-regulated compartment in the chassis; a locking bar pivotally attached to the chassis; a headwall mount attached to the chassis; a display mounted on the chassis; and a positionable task light attached to the chassis. Each drawer includes a drawer lock shiftable between a locked position and an unlocked position. The locking bar is shiftable between a locked position and an unlocked position so that the locking bar serves as a secondary safety lock for all the drawers and the door of the temperature-regulated compartment.

13 Claims, 16 Drawing Sheets

Related U.S. Application Data application No. 15/975,177, filed on May 9, 2018, now Pat. No. 10,188,477, which is a continuation-in-part of application No. 15/728,639, filed on Oct. 10, 2017, now Pat. No. 10,045,829.

(51) Int. Cl.

| | | |
|---|---|---|
| *A47B 31/02* | (2006.01) | |
| *A47B 67/04* | (2006.01) | |
| *A47B 81/00* | (2006.01) | |
| *A47B 96/18* | (2006.01) | |
| *A61B 50/36* | (2016.01) | |
| *A61B 90/35* | (2016.01) | |
| *A47B 96/20* | (2006.01) | |
| *A61G 12/00* | (2006.01) | |
| *A61M 5/14* | (2006.01) | |
| *A61B 50/33* | (2016.01) | |
| *G01G 17/00* | (2006.01) | |
| *G01G 19/42* | (2006.01) | |
| *A61B 50/00* | (2016.01) | |
| *A47B 31/00* | (2006.01) | |
| *A61B 50/18* | (2016.01) | |
| *A61B 50/30* | (2016.01) | |
| *G01G 17/04* | (2006.01) | |
| *G01G 21/28* | (2006.01) | |
| *A61B 90/96* | (2016.01) | |
| *A61B 90/94* | (2016.01) | |
| *A61B 90/98* | (2016.01) | |

(52) U.S. Cl.
CPC ............... *A47B 2220/0077* (2013.01); *A47B 2220/0091* (2013.01); *A61B 90/94* (2016.02); *A61B 90/96* (2016.02); *A61B 90/98* (2016.02); *A61B 2050/001* (2016.02); *A61B 2050/0014* (2016.02); *A61B 2050/0016* (2016.02); *A61B 2050/185* (2016.02); *A61B 2050/314* (2016.02); *A61G 2203/20* (2013.01); *A61G 2210/00* (2013.01); *A61M 2205/505* (2013.01); *G01G 17/04* (2013.01); *G01G 21/28* (2013.01)

(56) References Cited

U.S. PATENT DOCUMENTS

| | | | |
|---|---|---|---|
| 8,220,651 B2* | 7/2012 | Norcom | B65D 31/06 220/1.6 |
| 9,038,844 B2* | 5/2015 | Varbanov | B65D 21/0233 220/495.11 |
| 10,045,829 B1* | 8/2018 | Norman | A47B 67/04 |
| 10,376,617 B2* | 8/2019 | Giezendanner | G01F 22/00 |
| 2007/0106177 A1* | 5/2007 | Hama | A61M 1/0021 600/573 |
| 2008/0017194 A1* | 1/2008 | Hassanein | A61M 16/024 128/200.24 |
| 2008/0237239 A1* | 10/2008 | Pham | B65D 77/062 220/495.06 |
| 2010/0234665 A1* | 9/2010 | Soto | B08B 15/026 588/260 |
| 2014/0262553 A1* | 9/2014 | Pollock | G01G 17/04 177/1 |
| 2016/0095779 A1* | 4/2016 | Canady | A61B 50/15 280/79.2 |
| 2017/0274157 A1* | 9/2017 | Hendrix | G01G 19/52 |

\* cited by examiner

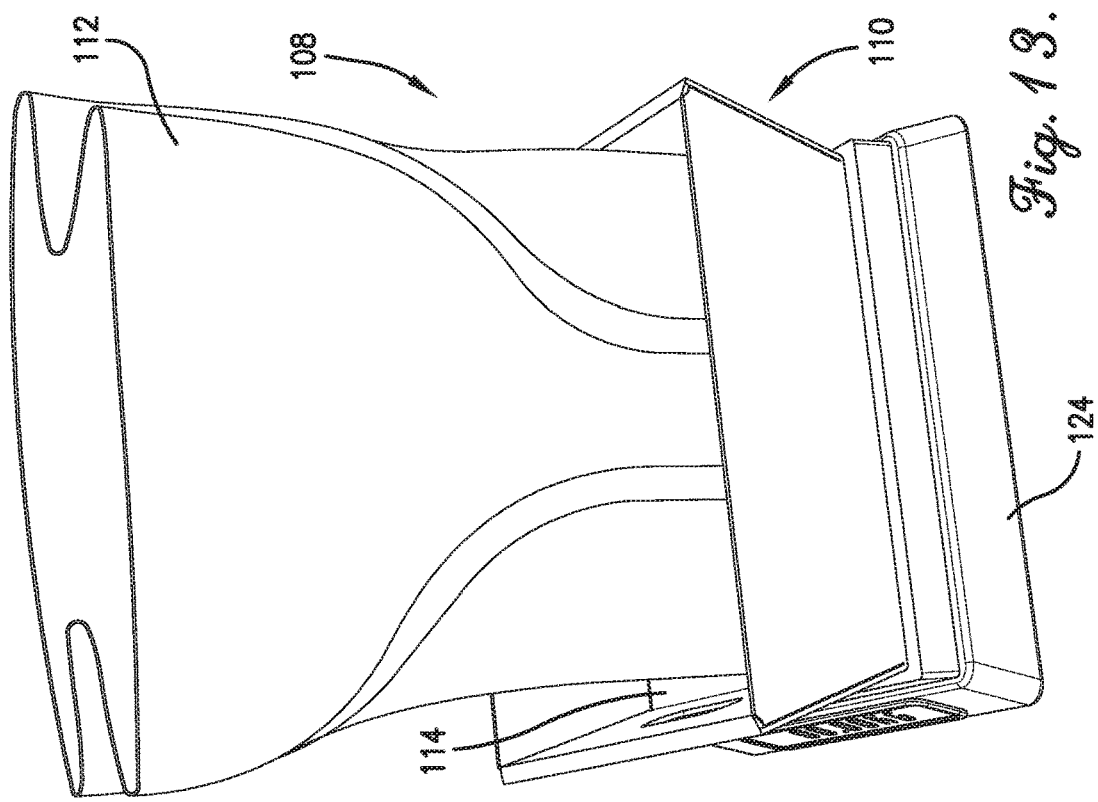
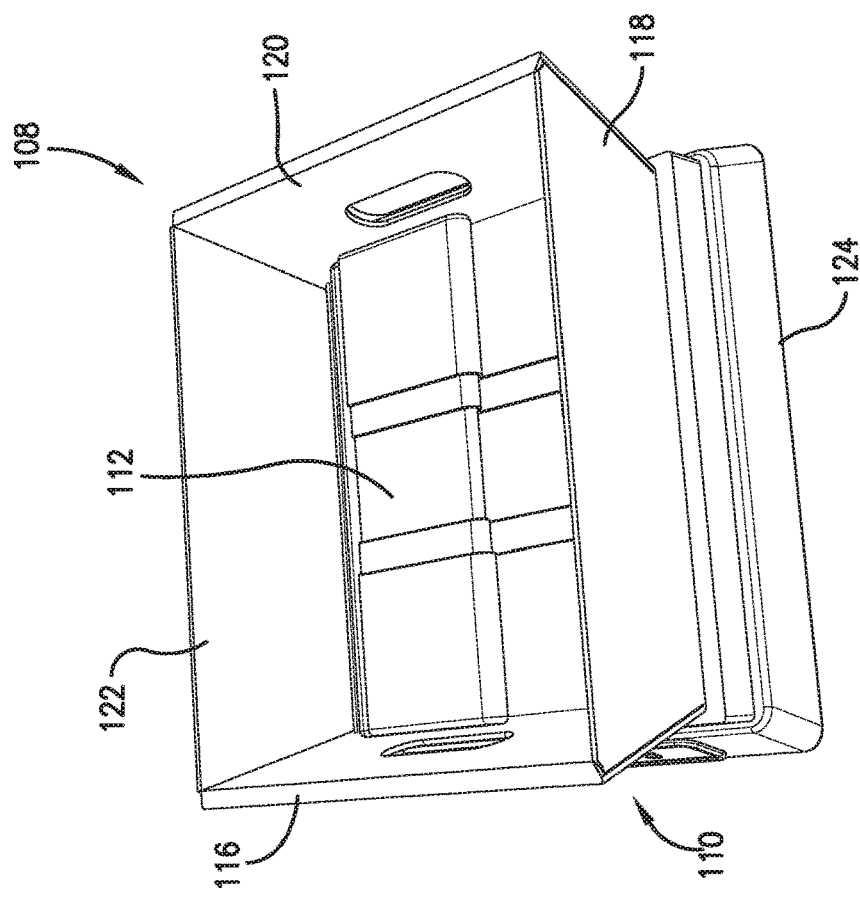

DISPOSABLE CONTAINER FOR MOBILE MEDICAL CART

RELATED APPLICATIONS

This patent application is a continuation of application Ser. No. 16/194,604, filed on Nov. 19, 2018, and entitled "DISPOSABLE CONTAINER FOR MOBILE MEDICAL CART", which is a continuation-in-part (CIP) of application Ser. No. 15/975,177, filed on May 9, 2018, and entitled "MOBILE MEDICAL CART", which is a continuation-in-part (CIP) of U.S. patent application Ser. No. 15/728,639, filed on Oct. 10, 2017, and entitled "OBSTETRIC HEMORRHAGE CART", now U.S. Pat. No. 10,045,829, issued Aug. 14, 2018. These previously filed applications are hereby incorporated by reference in their entireties into the present application.

BACKGROUND

Mobile carts for transporting various medical supplies, such as blood, pharmaceuticals, breast milk, etc., are commonly used in hospitals and other healthcare facilities. Such carts must often be configured to account for special handling requirements of particular medical supplies. For example, some medical supplies must be refrigerated, some are prone to theft, and others must be quickly accessed for emergencies.

Medical carts have been developed to try to address some of these requirements. For example, some carts include multiple compartments for storing and segregating different items, some carts include security features on the drawers for locking particular medical supplies in the carts to prevent theft, and other carts have refrigerated compartments for storing temperature-sensitive pharmaceuticals. However, no known cart addresses all of these requirements and others while still being portable and easily accessible for medical emergencies.

Medical waste such as blood-soaked pads and needles often must be collected and disposed during the use of the above-described medical carts. Plastic bags may be used for this purpose, but conventional bags are too flimsy for safely receiving and disposing hazardous items. This can be partially ameliorated by using bags as liners in rigid trash cans, but trash cans often don't fit on medical carts and must be washed and sanitized after every use.

Blood-soaked pads sometimes must be weighed during a medical procedure to estimate patient blood loss. Thus, some medical carts are equipped with weigh scales. But placing medical waste on weigh scales is unsanitary and necessitates frequent cleaning and sanitation of the scales.

This background discussion is intended to provide information related to the present invention which is not necessarily prior art.

SUMMARY

The present invention solves the above-described problems and provides a distinct advance in the art of mobile carts for healthcare environments and disposable containers for collecting, weighing, and disposing medical waste. More particularly, the present invention provides a versatile medical cart for diagnosis, analysis, and/or treatment that enables the storage and transportation of medical supplies in a highly-organized and secure manner. The invention also provides a disposable container that may be used to receive and weigh medical waste and then safely dispose of the medical waste.

A medical cart constructed according to one embodiment of the present invention broadly includes a chassis, a plurality of drawers, a temperature-regulated compartment, a locking bar, a headwall mount, a display, and a positionable task light. The chassis is provided for supporting the other components of the cart and includes a plurality of wheels attached thereto. The drawers are supported on the chassis and are provided for storing medical supplies. Each drawer includes a drawer lock shiftable between a locked position in which it prevents the drawer from opening and an unlocked position in which it allows the drawer to open.

The temperature-regulated compartment is also supported on the chassis for storing temperature-sensitive medical supplies. The temperature-regulated compartment includes a storage space with a door, a lock shiftable between a locked position in which it prevents the door from opening and an unlocked position in which it allows the door to open, and a temperature regulating unit that regulates a temperature of the storage space at a predetermined temperature.

The locking bar is pivotally attached to the chassis and acts as a secondary locking device for all the drawers and the temperature-regulated compartment to prevent unauthorized access to the drawers and temperature-regulated compartment. The locking bar is shiftable between a locked position in which it prevents the opening of all the drawers and the door of the temperature-regulated compartment and an unlocked position in which it allows the drawers to open when the drawer locks are in their unlocked positions and allows the door of the temperature-regulated compartment to open when the door lock is in its unlocked position.

The headwall mount is attached to the chassis for mounting items normally mounted on a bedside wall, such as suction cups, breast pumps, etc. The headwall mount has a vertically adjustable bar and a horizontal cross bar.

The display is mounted on the chassis for displaying information related to medical supplies stored in the medical cart or patient-related information.

The positionable task light is attached to the chassis and provides additional light for working around the medical cart. The positionable task light includes a deformable body portion and a light source.

A medical cart constructed in accordance with another embodiment of the invention also includes drawer mounts disposed inside the chassis and a plurality of interchangeable drawer slides attached to the plurality of drawers and removably attachable to the plurality of drawer mounts so that the drawer slides may be placed on different mounts, thereby allowing different-sized drawers to be mounted to the chassis. One of the drawers may support a weigh scale for weighing medical waste during or after a medical procedure.

Another aspect of the invention is a disposable container for use with the weigh scale. An embodiment of the disposable container includes a rigid, open-topped enclosure and a disposable hazardous waste bag attached to the enclosure.

The rigid enclosure serves as a base and support for the hazardous waste bag so the bag can more easily collect medical waste without tipping over. The enclosure is preferably formed of corrugated plastic but may be formed of any materials that are substantially water-proof and rigid. An embodiment of the enclosure is shaped as an inverted, truncated pyramid and has a planar floor and raised walls.

Non-skid rubber feet may be attached to the lower surface of the floor, so the enclosure doesn't slide on a weigh scale or other surface.

The bag is initially folded flat against the floor of the rigid enclosure and may be subsequently pulled out of the enclosure for collecting and disposing hazardous waste such as blood-soaked pads and needles. An embodiment of the hazardous waste bag comprises a closed end attached to the floor of the enclosure with adhesives, staples, rivets, or other fasteners and an open upper end that defines an opening for receiving medical waste in the bag. The bag is preferably formed of polyethylene but may be formed of any materials that are substantially water-proof and flexible.

The entire disposable container may be placed on a scale with the bag initially folded against the floor of the rigid enclosure. The bag may then be pulled out of the enclosure and then pulled down over the sides of the enclosure and the scale to cover the scale and protect it from medical waste placed in the bag. The bag may have a transparent portion that aligns with the display of the scale, so the display may be read through the bag. Embodiments of the bag may also have grommets or other fasteners for connecting to hooks or other connections points on the medical cart, so the bag can cover and shield the medical cart from medical waste placed in the bag.

During or after a medical procedure, the weight of the container and its contents may be noted to estimate patient blood loss. Specifically, the unfilled weight of the container itself and the dry weight of any pads, sponges, etc. placed in the container are subtracted from the filled weight of the container to estimate the weight of blood soaked in the pads, sponges, etc.

At the completion of the medical procedure, the upper end of the bag may be pulled up and closed to seal the medical waste in the bag. The entire container, including the rigid base, hazardous waste bag, and all the contained medical waste, may then be discarded in a safe and sanitary manner.

The hazardous waste bag may further comprise a closure mechanism for sealing its upper end to contain the medical waste in the bag for safe disposal. The closure mechanism may be interlocking grooves and ridges formed in the upper end of the bag that may be pressed together to close and seal the bag, a drawstring, tape, adhesives, or anything else that can close and seal the bag.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 12 is a perspective view of a disposable container constructed in accordance with another embodiment of the invention and shown supported on a weigh scale associated with the cart of FIG. 1;

FIG. 13 is a perspective view of the disposable container of FIG. 12 showing its bag being raised out of its enclosure;

Figure 1:
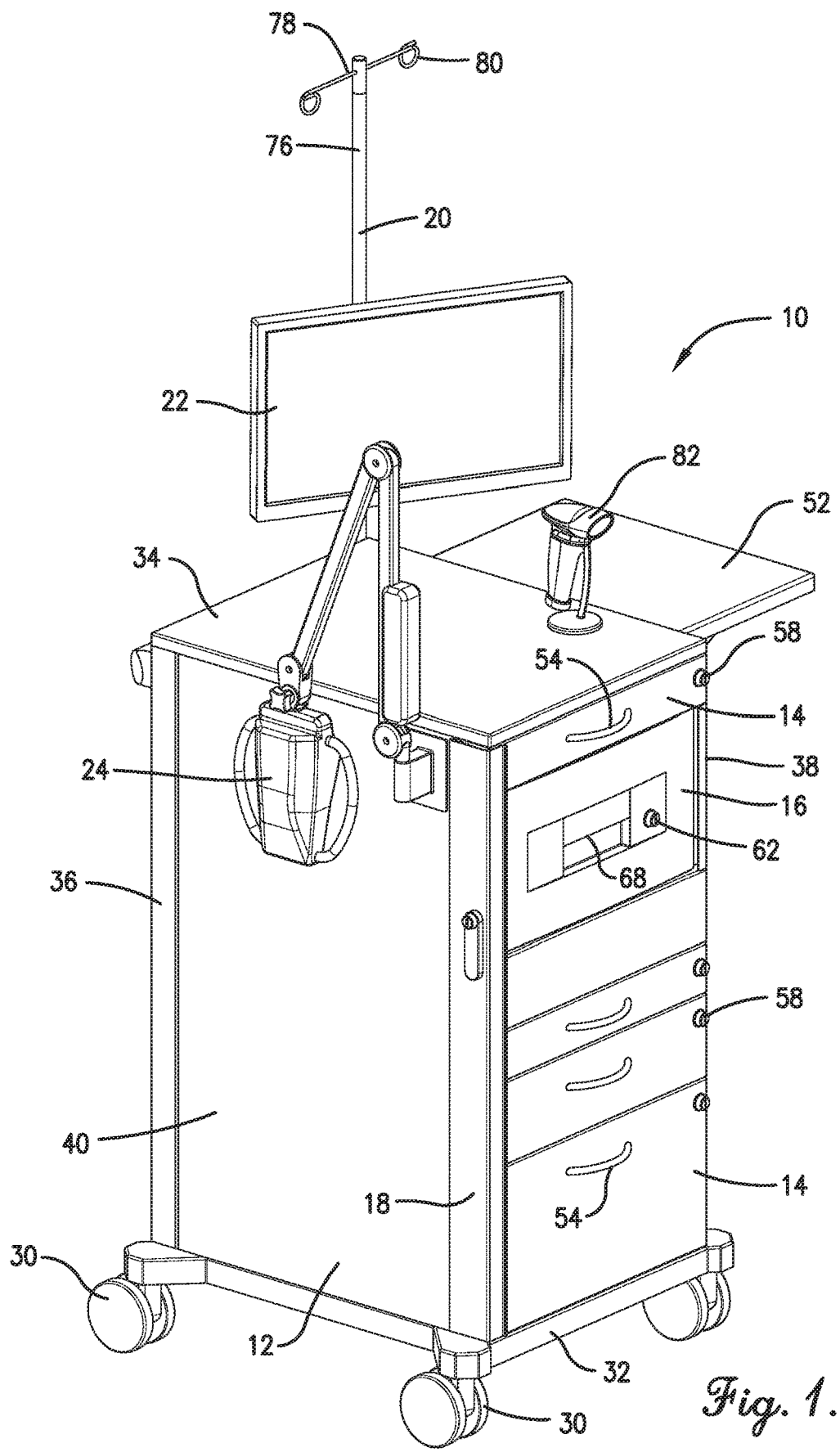
FIG. 1 is a perspective view of a cart constructed in accordance with an embodiment of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the present technology can include a variety of combinations and/or integrations of the embodiments described herein.

Turning now to the drawing figures, and particularly FIG. 1, a medical cart 10 constructed in accordance with a preferred embodiment of the invention is illustrated. The cart 10 constructed in accordance with this embodiment may broadly include a chassis 12, a plurality of drawers 14, a temperature-regulated compartment 16, a locking bar 18, a headwall mount 20, a display 22, a positionable task light 24, and a power source 26 (shown in FIG. 9).

Figure 7:
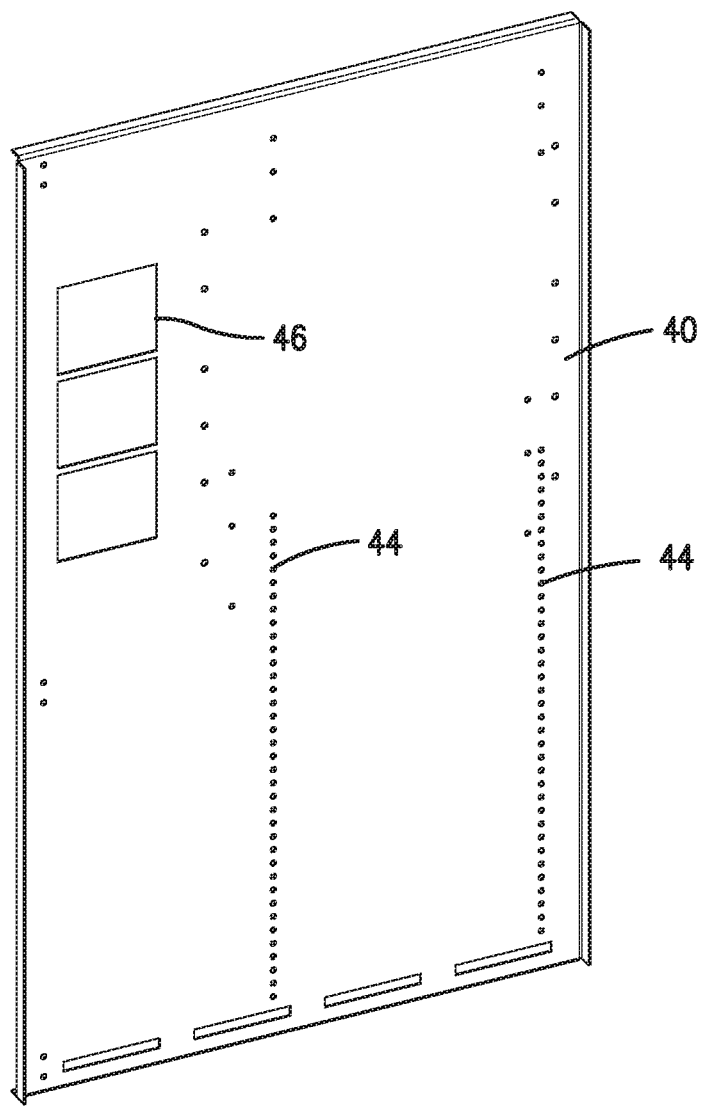
FIG. 7 is a side perspective view of a side wall of the cart of FIG. 1, illustrating mounting holes and ventilation holes formed therethrough.

The chassis 12 may include a frame 28 and a plurality of wheels 30 on which the frame 28 may travel. The frame 28 may be configured for attaching various components of the cart 10. For example, the frame 28 may include a base 32, a top surface 34 opposite the base 32, a back wall 36, an opposing front wall 38, and two opposing side walls 40, 42, all of which may join to enclose a space within the chassis 12. In some embodiments of the invention, as illustrated in FIG. 7, the side walls 40, 42 may include a plurality of mounting holes 44 and ventilation holes 46, allowing reconfigurability or customization of the drawers 14, using any quantity and size of drawers 14. The plurality of ventilation holes 46 can likewise allow the temperature-regulated compartment 16 to be repositioned along a height of the chassis 12, while still providing an opening through which hot air from the temperature-regulated compartment 16 may be expelled. In some embodiments of the invention, at least one of the side walls 40, 42 may include an outer panel and an inner panel spaced apart from each other, with the inner panel including the ventilation holes 46 such that heat expelled from the temperature-regulated compartment 16 through the ventilation holes 46 is forced between the inner and outer panels and exits into the space within the chassis 12 through one of the other holes along the inner panel, above or below the temperature-regulated compartment 16.

Figure 3:
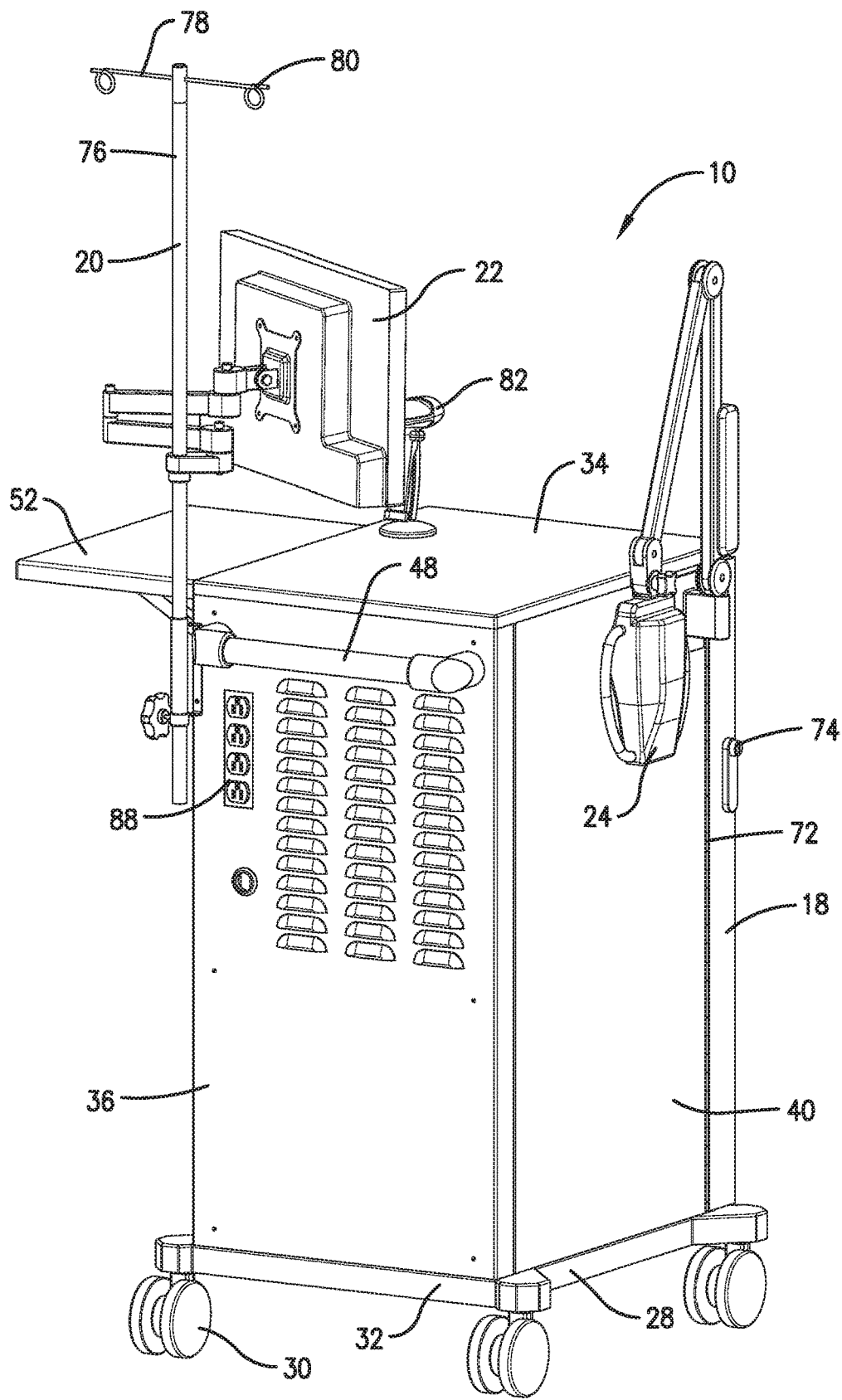
FIG. 3 is a side elevation view of the cart of FIG. 1.
Figure 4:
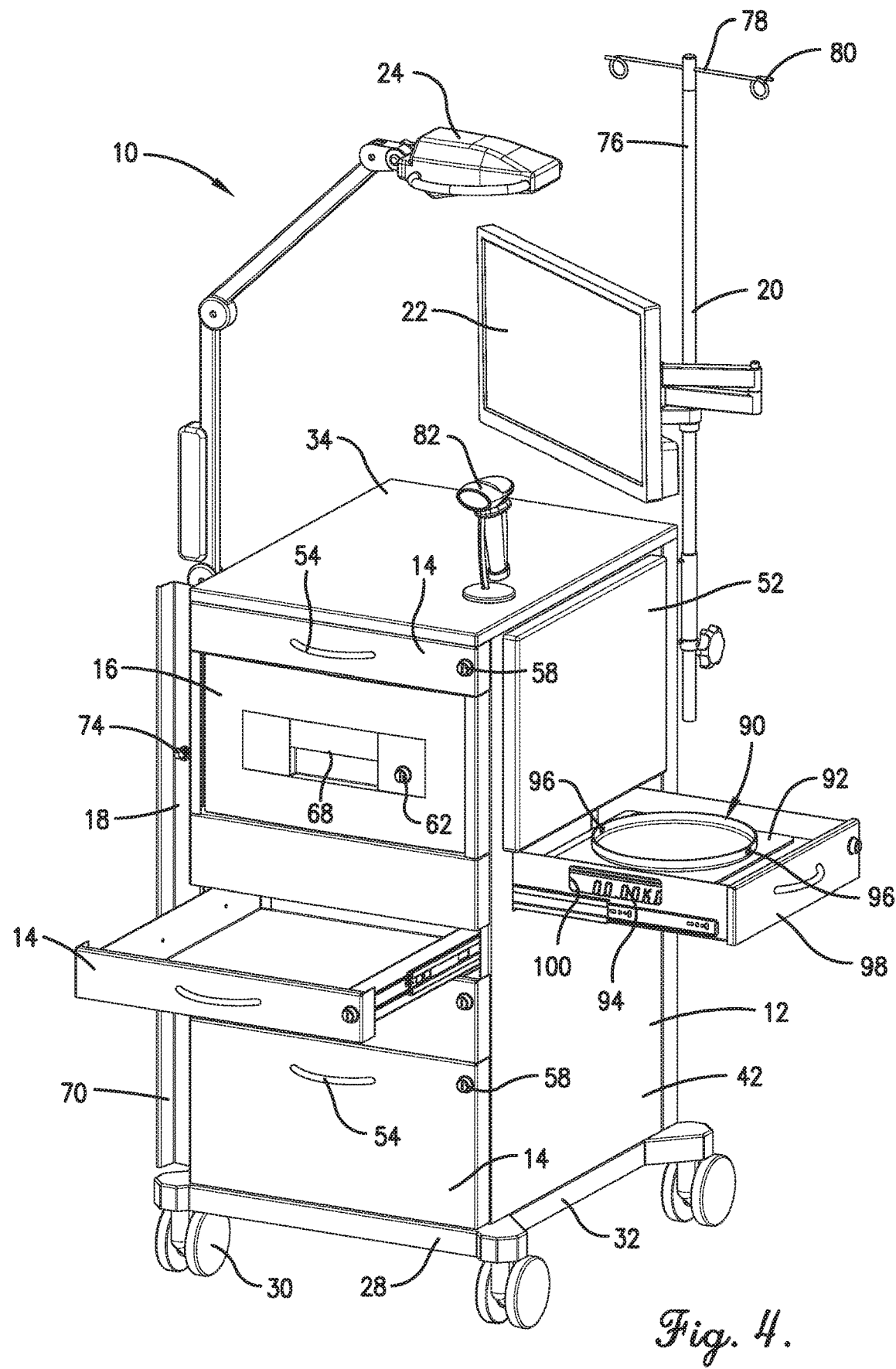
FIG. 4 is a front elevation view of the cart of FIG. 1 with a scale drawer in an open position.
Figure 8:
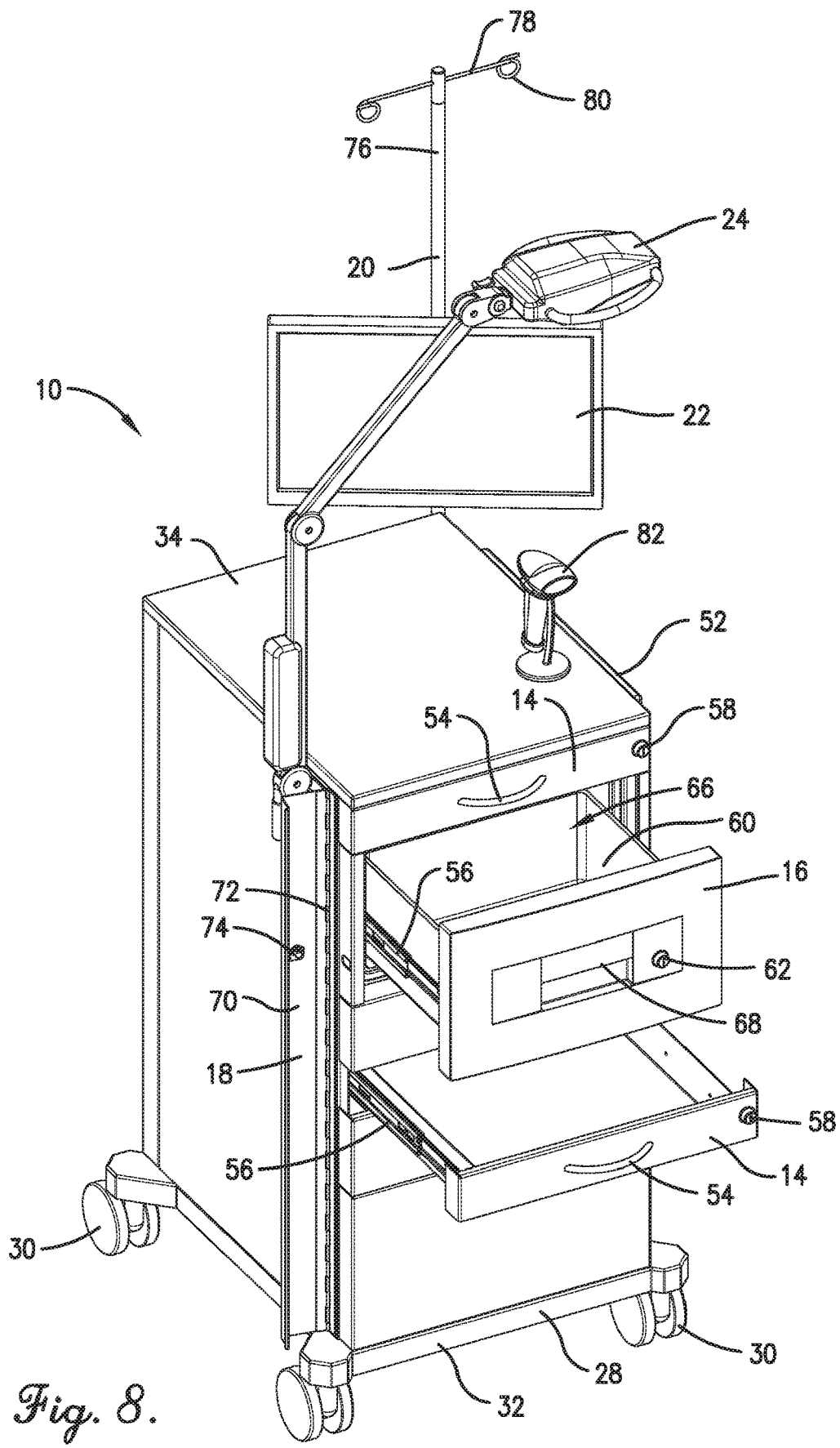
FIG. 8 is a front perspective view of the cart of FIG. 1 with a locking bar pivoted to a disengaged position.

The front wall 38 and at least one of the side walls 40, 42 may have one or more openings formed therein, allowing the drawers 14 to slide into and out of the chassis 12, as well as providing access to the temperature-regulated compartment 16, as shown in FIGS. 4 and 8. The plurality of wheels 30 may include four wheels and may be attached to the base. However, the chassis 12 may include any quantity of wheels without departing from the scope of the invention. In some embodiments of the invention, as illustrated in FIG. 3, the chassis 12 may also include a handle 48 attached to one of the side walls 40, 42, the front wall 38, and/or the back wall 36.

Figure 2:
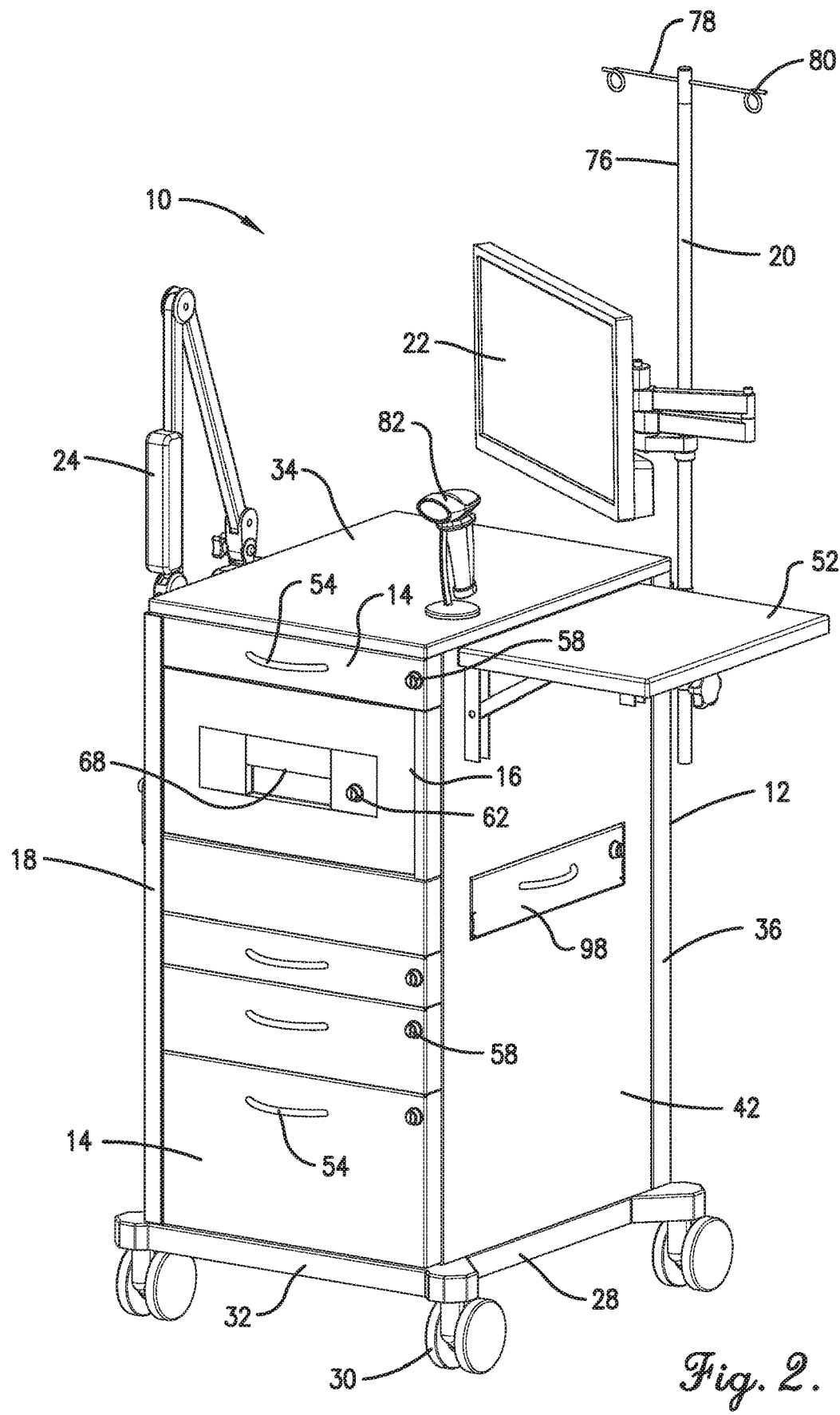
FIG. 2 is a front elevation view of the cart of FIG. 1.
Figure 5:
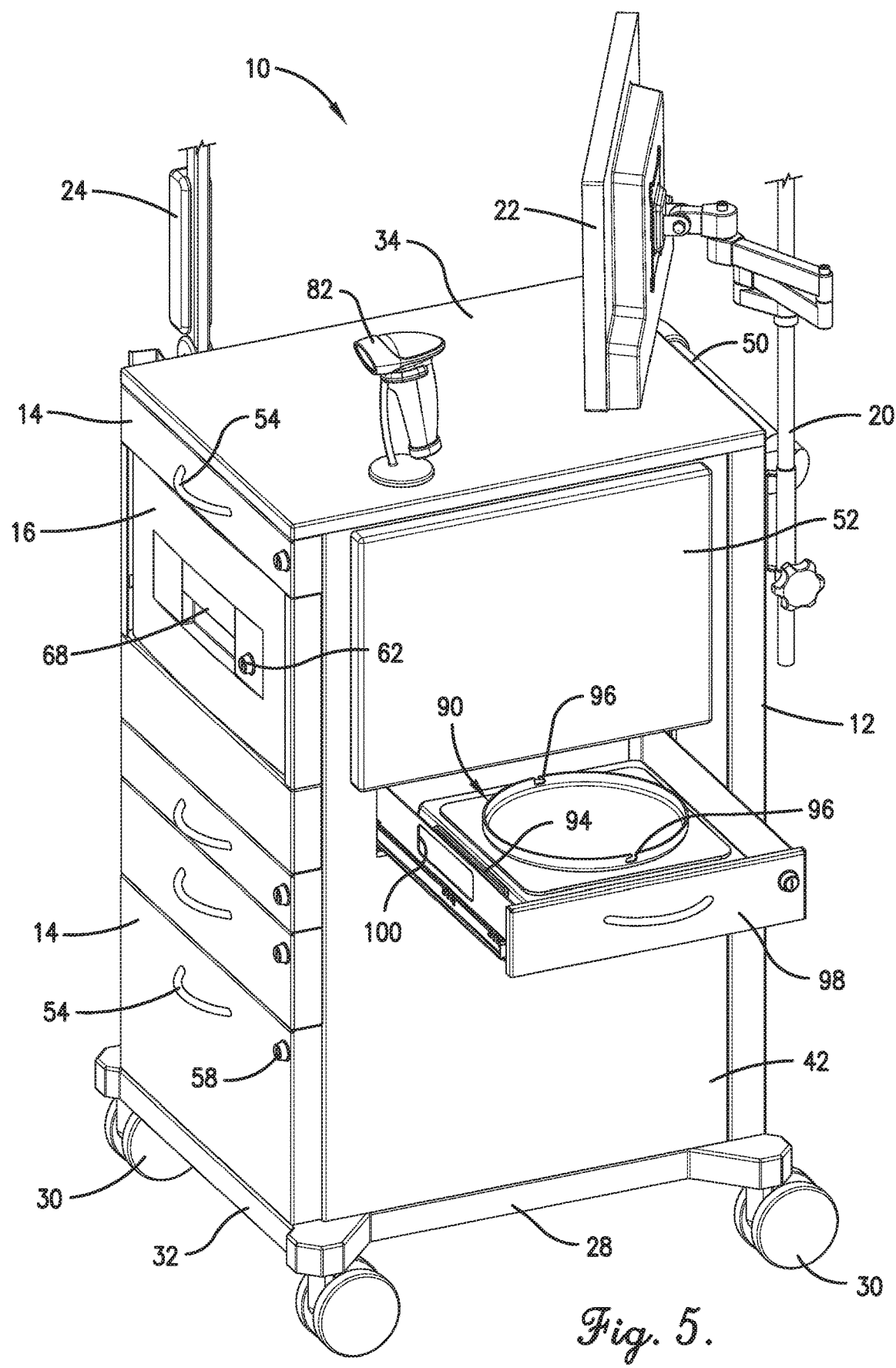
FIG. 5 is a top plan view of the cart of FIG. 4 with the scale drawer open.
Figure 9:
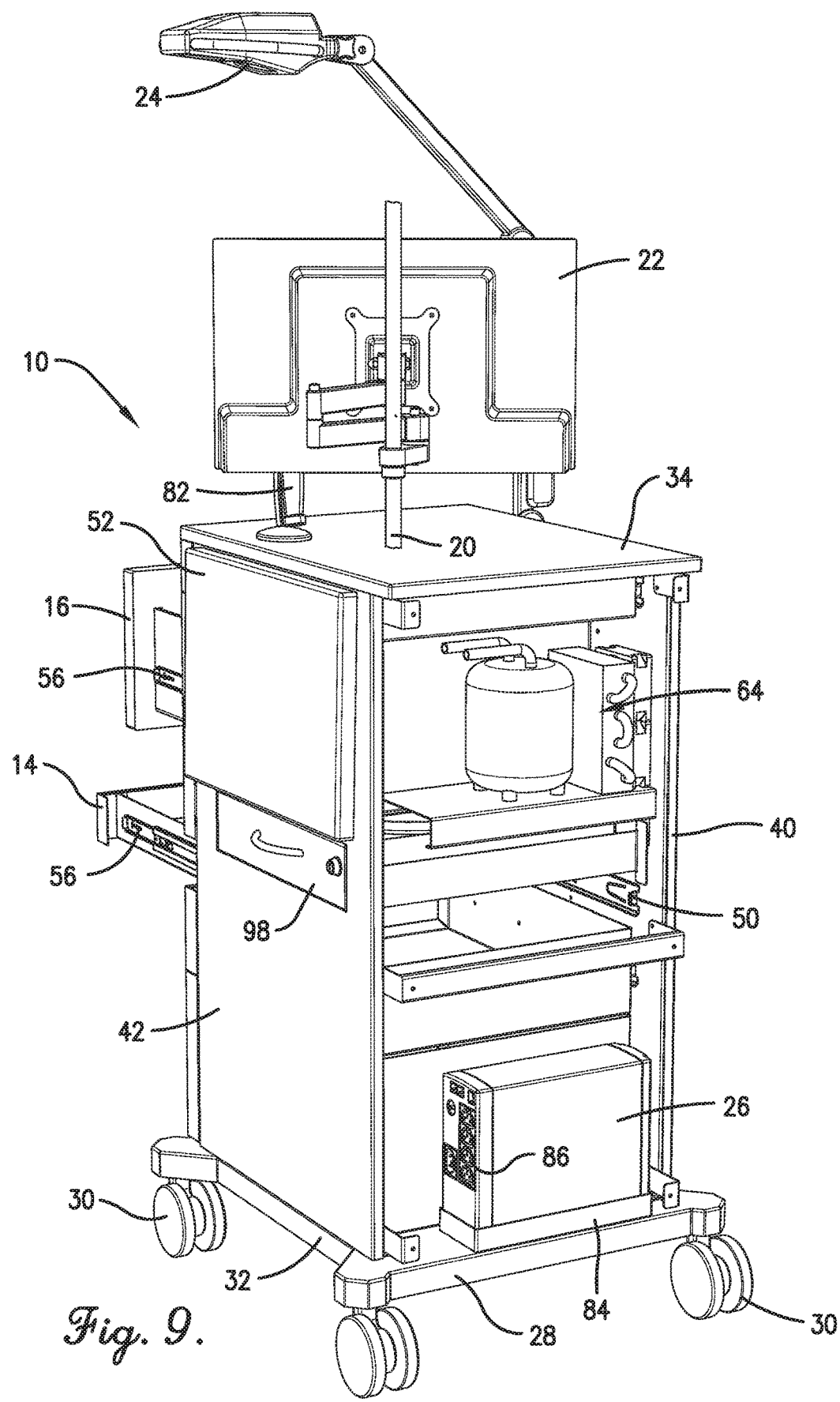
FIG. 9 is a back perspective view of the cart of FIG. 1.

As illustrated in FIG. 9, the chassis 12 may further comprise drawer mounts 50 installed within the frame 28, such as along interior surfaces of the front, back, or side walls 36, 38, 40, 42 and/or along the base 32 or top surface 34 of the frame 28. Specifically, the drawer mounts 50 may be installed in any combination along a height of the chassis 12. The drawer mounts 50 may have a uniform height between each pair of drawer mounts 50, or the drawer mounts 50 may have different heights between each pair of drawer mounts 50. The drawer mounts 50 may include rails, ledges, or other protrusions or depressions sized, shaped, and oriented for supporting the drawers 14 and/or allowing the drawers 14 to slide into and out of the chassis 12. For example, the drawer mounts 50 may include rails that are screwed into or otherwise anchored to the holes 44 formed into the side walls 40, 42 of the chassis 12, as described above. By screwing the drawer mounts 50 into a different set of the side wall holes 44, the drawers 14 of the cart 10 may be reconfigured or exchanged for different sizes of drawers 14. A side wall 40, 42 may also include a procedure shelf 52 pivotably attached to the side wall 40, 42. As shown in FIG. 2, the procedure shelf 52 may fold out to provide a surface next to the top surface 34 of the frame 28. The procedure shelf 52 may also fold down positioned in a downward direction as shown in FIG. 5.

One or more surfaces of the chassis 12, such as the top surface 34, handle 48, or procedure shelf 52 may be constructed of antimicrobial material and/or completely or partially coated with an antimicrobial material. The antimicrobial material may be any material that inhibits the growth of pathogenic microorganisms such as bacteria, fungi, yeast, algae, mold, and/or viruses, etc. The material may be a metal such as copper, silver, gold, etc., or an alloy such as brass, bronze, cupronickel, copper-nickel-zinc, or others. Additionally, or alternatively, the material may be polymers, polymeric biocides, organosilanes, or the like. In some embodiments of the invention, an underside of the top surface 34 of the chassis 12 may have a notch formed or molded therein, into which a locking mechanism may extend for locking a top-most one of the drawers 14 or temperature-regulated compartment 16.

The drawers 14 are provided as storage compartments for the various medical supplies such as medications, intravenous fluids, blood for transfusions, a portable ultrasound machine, and/or scales. The drawers 14 may each include a front wall, a back wall, opposing side walls, and a bottom wall forming a container with an open top through which supplies may be accessed. The drawers 14 may each also include a handle 54 attached to or integrally formed with the front wall thereof. Furthermore, the drawers 14 may each include drawer slides 56. The drawer slides 56 may be attached to exterior surfaces of the side walls of the drawers 14 and may be configured to slidably engage the drawer mounts 50 installed in the chassis 12. Specifically, the drawer slides 56 may include wheels, rails, protrusions, indentions, or other elements configured for slidably engaging with the drawer mounts. When one of the drawers 14 is slid into an open orientation, a user may access supplies therein through the open top thereof. Likewise, when one of the drawers 14 is slid into a closed orientation, a user is prevented from accessing supplies therein through the top thereof. In some embodiments of the invention, the drawer mounts 50 and drawer slides 56 may be configured to be interchangeable so that any drawer slide 56 can slidably engage any drawer mount 50, allowing for a variety of drawer sizes and configurations.

In some embodiments of the invention, one or more of the drawers 14 may include a lock 58. The lock 58 may be shiftable between a locked and unlocked position. When the lock 58 is in the locked position, it prevents its drawer 14 from opening. When in the unlocked position, the lock 58 allows its drawer 14 to open. The lock 58 may be any locking mechanism, such as a lock-and-key system, a digital lock, a magnetic lock, or any drawer-locking device known in the art for preventing unauthorized access to one or more of the drawers 14.

The temperature-regulated compartment 16 may be provided for storing medical items that have temperature-related sensitivities, such as containers of blood for transfusions, intravenous fluids, prescription drugs, or other medication. The temperature-regulated compartment 16 may include a storage space 60, a lock 62, temperature-regulating unit 64 such as a heating unit and/or a cooling unit, and drawer slides 56. The drawer slides 56 of the compartment 16 are interchangeable like the drawer slides 56 of the drawers 14 so that a user can insert the temperature-regulated compartment 16 in different configurations according to his or her requirements. For example, the cart 10 could have a single compartment 16, multiple compartments 16, or none. Alternatively, the temperature-regulated compartment 16 may include an open front, a door 66 openable for accessing items in the temperature-regulated compartment 16.

The heating unit may be any type of device that increases the temperature of the space in the compartment 16, such as a radiator, heat exchanger, heating element, fan, filament, and the like. The cooling unit may include a compressor, condenser coils, evaporator coils, fans, pipes, valves, a thermostat for keeping the storage space 60 within a predetermined tolerance of user-selected temperature, and the like. In some embodiments of the invention, the temperature-regulated compartment 16 may additionally or alternatively include a freezer or any other cooling compartment known in the art for cooling supplies therein. Some components of the temperature-regulated compartment 16 may be electrically coupled to the power source, providing electrical power for operation thereof.

The door 66 may be pivotally attached to the storage space 60 or may include a drawer shiftable between an open and a closed position. For example, the door 66 may be a drawer including a front wall with a handle 68 attached thereto or integrally formed therewith, a back wall opposite the front wall, two opposing side walls extending between the front and back walls thereof, and a bottom wall, cooperatively forming a container with an open top. The lock 62 is shiftable between a locked position and an unlocked position. In the locked position, the lock 62 may prevent the door 66 from opening, while in the unlocked position, the lock 62 may allow the door 66 to open. The lock 62 may be any locking mechanism known in the art, such as a lock-and-key system, a digital lock, a magnetic lock, or any locking device known in the art for preventing unauthorized access to contents within the storage space 60 of the temperature-regulated compartment 16.

The locking bar 18 is provided as an additional security measure for securing all the drawers 14 and temperature-regulated compartments 16 in their closed positions. The locking bar 18 may include a flange 70, hinges 72, and a locking mechanism 74. The flange 70 may be a long, flat strip of rigid material or may be a long, right-angled strip of rigid material. The flange 70 may substantially extend an entire height of the chassis 12 or otherwise span a distance of a plurality of the drawers 14 and/or the temperature-regulated compartment 16. In some embodiments, the flange 70 may be pivotally attached at or proximate to a corner of the chassis 12 where one of the side walls 40, 42 connects with the front wall 36. The flange 70 may be pivotally attached to the chassis 12 via the hinges 72, and may be pivotally actuatable between a blocking orientation blocking the drawers 14 and the temperature-regulated compartment door 66 from opening, and a non-blocking orientation that does not block the drawers 14 and temperature-regulated compartment door 66 from opening. The hinges 72 may be any jointed or flexible mechanical device known in the art for allowing pivoting about a pivot point. Additionally or alternatively, in some embodiments of the invention, the locking bar 18 may be pivotally attached to a rod or rigid elongated cylinder and pivots about an axis thereof.

The locking mechanism 74 may include a lock-and-key system, a digital lock, a keypad, a magnetic lock, and/or any device known in the art for selectively preventing pivoting of the flange 70 about the hinges 72. For example, the locking mechanism 74 may be any keypad known in the art, such as a digital keypad, a combination lock, a set of combination discs, or the like. The locking mechanism 74 may be actuatable between an engaged position and a disengaged position using a key, keycard, security code, mechanical actuation, or the like. The flange 70 may freely pivot toward and away from the drawers 14 and the front wall 36 of the chassis 12 about the hinges 72 when the locking mechanism 74 is in the disengaged position. When the flange 70 is pivoted flush against front walls of the drawers 14 and the front wall 36 of the chassis 12, the locking mechanism 74 may be placed into the engaged position, such that the flange 70 is prevented from pivoting. Likewise, when the locking mechanism 74 is engaged and the flange 70 is prevented from pivoting, the drawers 14 and/or the temperature-regulated compartment door 66 are all simultaneously prevented from opening.

The headwall mount 20 may be provided for hanging various medical items such as suction cups, breast pumps, IV fluid bags, and other medical items normally supported on a free-standing pole in hospital rooms. The headwall mount 20 may include a primary pole 76 fixed to the chassis 12, a crossbar 78 fixed at or proximate to a top of the primary pole 76, and one or more hooks 80 onto which IV bags or the like may be attached. The headwall mount 20 may be vertically adjustable via a height adjustment mechanism, such as a telescoping mechanism or other mechanical elongation or actuation mechanisms known in the art. For example, the primary pole 76 may include a top portion slidably actuatable relative to a bottom portion fixed to the chassis 12.

The display 22 may be provided for presenting information to a user. The display 22 may be fixed or adjustably attached to the chassis 12 or the headwall mount 20 and may be configured for receiving signals from the portable ultrasound machine via a communication cable or other wireless communication devices. In general, the display 22 may comprise an electronic graphical interface operable to display visual graphics, images, video, text, etc. in response to external or internal processes and commands. For example, the display 22 may comprise conventional black and white, monochrome, or color display elements including CRT, TFT, LCD, and/or LED display devices. Further, the display 22 may comprise wired or wireless data transfer elements and/or communication ports such as a removable memory, data transceivers, or the like, to enable the user and other devices or parties to communicate with the display 2. In particular, the display 22 may include one or more ports configured for receiving and/or sending data from and to the portable ultrasound machine or other electronic devices configured to output displayable graphics, video, or other information.

The information may be related to a patient or group of patients, the medical supplies stored in the cart 10, the open/closed status of the drawers 14 or temperature-regulated compartments 16, the locked/unlocked status of the drawer locks 58 or compartment locks 62 or the locking bar 18, the temperature inside any temperature-regulated compartments 16, or any other information a user requires. The display 22 may include a port for connecting to various devices, a user interface, a communication element, and a connector for connecting the display 22 to the power source 26. The display 22 may be embodied as a personal computer such as a desktop workstation and/or laptop computer, smartphone, a tablet computer, phablet, wearable electronic, or the like.

The user interface may comprise one or more functionable inputs such as buttons, switches, scroll wheels, a touch screen associated with the display 22, voice recognition elements such as a microphone, pointing devices such as mice, touchpads, tracking balls, styluses, cameras such as a digital still or video camera, combinations thereof, or the like. For example, the display 22 may include or may be integrated with a touch screen display configured to enable a user to interact with the display by touching or pointing at display areas to provide information, make selections, and/or label something on the screen. In some embodiments of the invention, the user interface of the display 22 may comprise a pointer (e.g., stylus). Specifically, a position and orientation of the pointer may be tracked, as later described herein, so that when a user points at a particular area on the display, corresponding markings or labeling may be presented on the display 22.

In some embodiments, the user may also input information through a scanner 82, as shown in FIG. 1. The scanner 82 may be provided for scanning objects such as medical supplies, RFID tags, bar codes, QR codes, hospital wristbands, and the like. The scanner 82 scans one of the objects, extracts information embedded on the object, and transmits it to the display 22. In some embodiments, the scanner 82 may utilize wired or wireless communication with the display 22.

The task light 24 may be any light adjustably fixed to the chassis 12, and may be articulated to a particular height, angle, and orientation to assist medical personnel. The task light 24 may include a light bulb, electrical cords or connectors providing electricity from the power source 26 to the lightbulb, and an adjustable, jointed, and/or bendable light stand fixed to the chassis 12. For example, the task light stand may include three or four articulating joints for positioning the task light 24 as needed during procedures. The task light stand may be fixed to the chassis 12 at or proximate to the back wall 36 thereof, and/or at or proximate to one of the side walls 40, 42 thereof.

The power source 26 may include one or more rechargeable batteries, a capacitor, an uninterruptible power supply (UPS), or the like. The power source 26 may be electrically coupled with the task light 24, the temperature-regulated compartment 16, and the display 22, as well as other sensors, displays, and medical devices incorporated into the cart 10. For example, the power source 26 may also be electrically coupled with a portable ultrasound machine to provide power thereto. The power source 26 may be positioned within the chassis 12 and may be secured in a tray 84 mounted to the base 32 of the chassis 12, between the drawers 14 and the back wall 36 of the chassis 12. The power source 26 may include a plurality of outlets 86 configured for receiving standard electrical plugs, such that the temperature-regulated compartment 16, task light 24, display 22, and the like may be plugged directly therein. Furthermore, a power strip 88 or other collection of power outlets may be plugged into or electrically coupled to the power source 26 and then fixed and presented through an opening of the back wall 36 of the chassis 12, such that other electrical tools or accessories, beyond those integrated into the cart 10, may access the power source 26 as needed.

In some embodiments of the present invention, the cart 10 may further include a scale 90. The scale 90 may be any scale known in the art with a scale-weighing surface 92 and a digital or mechanical display 94 configured to output the weight of any solid or liquid placed on the scale weighing surface 92. The scale 90 may generally have an overall low profile to allow the scale 90 to fit within one of the drawers 14. In some embodiments of the invention, the scale weighing surface 92 may be a flat square, rectangular, or circular platform. However, the scale 90 may have other shapes and configurations without departing from the scope of the invention. In some embodiments of the invention, the scale-weighing surface 92 may include a clamping device 96 for an open topped-enclosure, or alternatively may include a bowl, container, or protruding platform edges configured for preventing blood from dripping off sides of the scale-weighing surface.

The scale 90 may be mounted in one of the supply drawers 14, described above, referred to hereinafter as a scale drawer 98. The scale drawer 98 may extend outward through an opening in one of the side walls 40, 42 of the chassis 12, such that other drawers 14 are not blocked while the scale 90 is being accessed, as shown in FIG. 5. For example, one of the drawers 14 may slide in and out of the chassis 12 along a first axis and the scale drawer 98 may slide in and out of the chassis 12 along a second axis that is substantially perpendicular to the first axis. The scale's low profile prevents the scale 90 from interfering with opening or closing of the scale drawer 98. The scale drawer 98 may include a translucent sidewall, a window 100, or an opening formed therethrough, providing a window viewable from the front of the chassis 12 when the scale drawer 98 is open. This allows a user to view the scale's display 94 during use, while the scale 90 remains in the open scale drawer 98. Alternatively, the scale 90 may be electrically coupled with a remote display (not shown) mounted or integrated into the front wall 38 of the chassis 12 or a front wall of one of the drawers 14 without departing from the scope of the invention, such that the scale drawer 98 does not require the window 100 or translucent sidewall in order to read the scale 90 reading. In other embodiments of the invention, the scale 90 may communicate directly or wirelessly with other electronic devices or displays, transmitting the weight sensed by the scale thereto, without departing from the scope of the invention.

Different-sized drawers 14 may be inserted on the cart 10, depending on specific needs or preferences. For example, larger drawers, smaller drawers, or a combination of the two may be selected for particular uses. A temperature-regulated compartment 16 having a heating unit may be placed directly above a temperature-regulated compartment 16 having a cooling unit to take advantage of heat rising from the cooling unit. By using the generated heat rising from the cooling unit, the heating unit need not be activated as much and therefore uses less energy.

The cart 10 may be used while the power source 26 is plugged into a wall outlet or may be disconnected from the power source 26 and moved elsewhere. Even when disconnected, the power source 26 provides power to the compartments 16, the display 22, the task light 24, and any other device requiring power.

The drawers 14 and temperature-regulated compartments 16 may be secured by placing their respective locks 58, 62 in the locked position. The user may further secure the drawers 14 and temperature-regulated compartments 16 by placing the locking bar 18 in the locked position. Alternatively, for efficiency purposes, the user may keep the respective locks 58, 62 of the drawers 14 and temperature-regulated compartments 16 in their unlocked positions for quick access, while maintaining one level of security by placing the locking bar 18 in its locked position. The user may access the contents within a drawer 14 or temperature-regulated compartment 16 by unlocking the locking bar 18, and then unlocking the lock 58, 62 of the drawer 14 or temperature-regulated compartment 16 having the desired contents.

Medical supplies may be loaded into the drawers 14 or temperature-regulated compartments 16 by scanning a barcode, RFID tag, or QR code located on that item using the scanner 82. The information received by the scanner 82 is then displayed on the screen, and may include storage instructions, shelf-life, expiration date, intended patient, prescribing doctor, or the like. The item may then be placed in a drawer 14 or temperature-regulated compartment 16 based on that information. The item may be designated as "checked in" via the user interface or an input device. The electronic device 22 may then communicate with an external device that the item is checked in on that cart 10. An item may be "checked out" by removing it from its drawer 14 or temperature-regulated compartment 16, scanning it with the scanner 82, and reviewing the information received by the scanner 82 as displayed on the display 22. The item may then be delivered based on that information.

Figure 6:
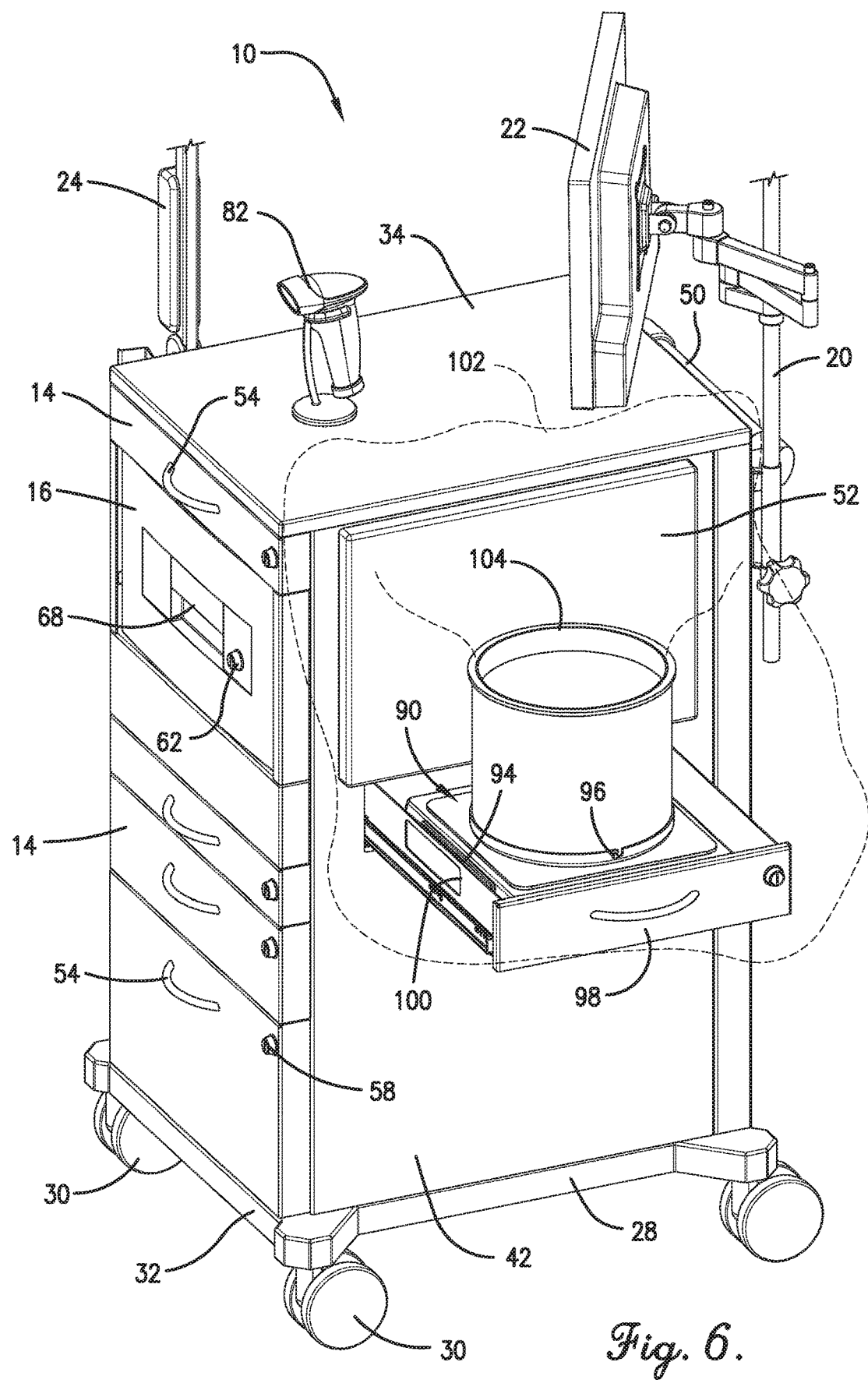
FIG. 6 is a top plan view of the cart of FIG. 4 with the scale drawer open and a disposable container mounted thereon.
Figure 10:
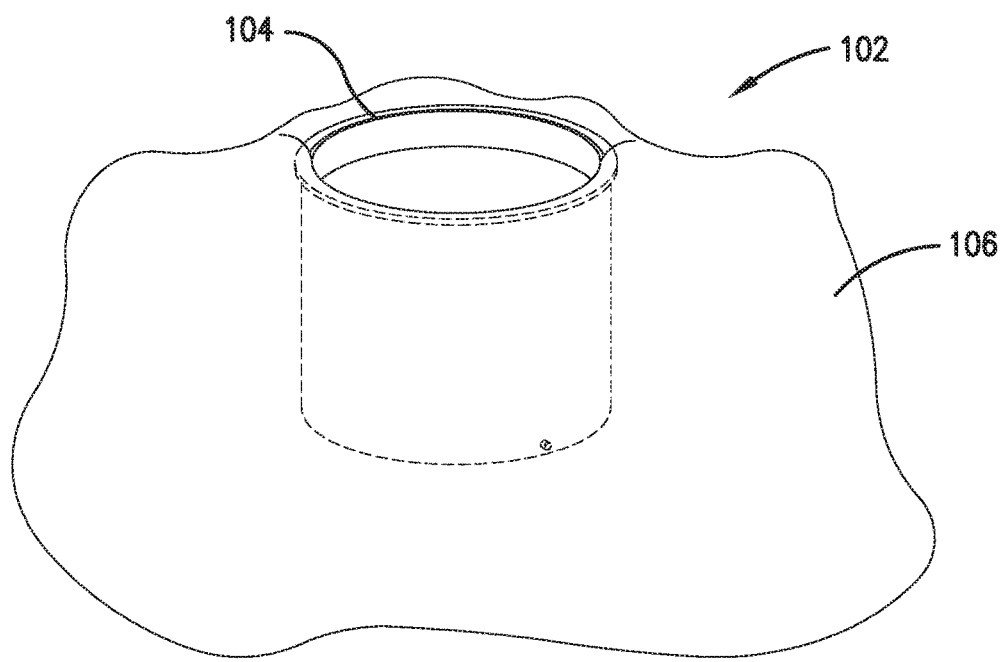
FIG. 10 is a front perspective view of a disposable container for use with the scale of FIG. 4, including a bag welded to and extending outward around an open-topped enclosure for receiving materials to be weighted by the scale.
Figure 11:
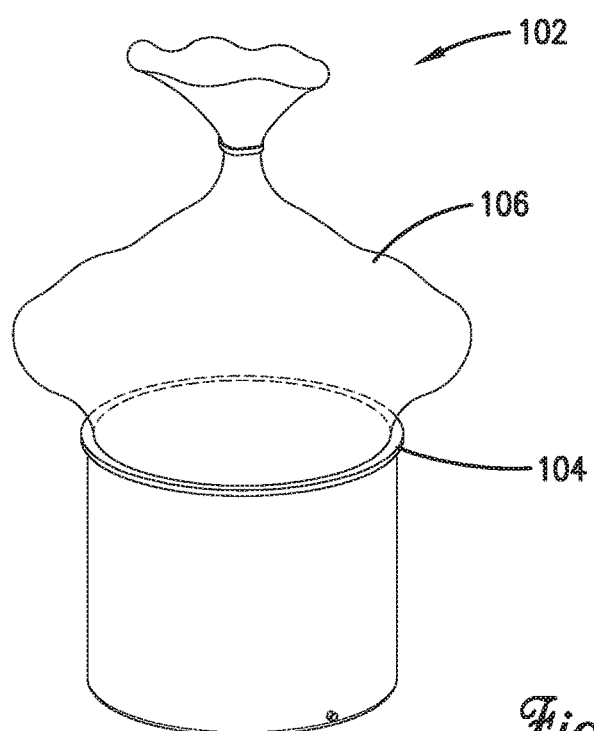
FIG. 11 is a front perspective view of the disposable container of FIG. 11 with the bag pulled upward and tied up for disposal.

In some embodiments of the invention, the cart 10 may be equipped with a disposable container 102 for receiving and disposing medical waste. The container may include an open-topped enclosure 104, such as a tray or bucket, and a disposable hazardous waste bag 106 integral with the open-topped enclosure 104, as shown in FIGS. 6, 10, and 11. A bottom end of the bag 106 may be welded along a top edge of the open-topped enclosure 104, with the remainder of the bag 106 initially contained inside the open-topped enclosure 104. The open-topped enclosure 104 may be attached to the scale weighing surface 92 after the scale drawer 98 is pulled out. This attachment may be accomplished using the clamping device 96, a locking mechanism, integrally-formed attachment components or protrusions, or any mechanical attachments known in the art, so that the open-topped enclosure 104 does not move during procedures. For example, the scale weighing surface 92 may include an upward-protruding clamping device sized and shaped to lock and secure the open-topped enclosure 104 to the scale weighing surface 92.

A disposable container 108 constructed in accordance with another embodiment of the invention is illustrated in FIGS. 12-15. The disposable container 108 broadly includes a rigid, open-topped enclosure 110 and a flexible hazardous waste bag 112 supported within and attached to the enclosure.

The rigid enclosure 110 serves as a base and support for the bag 112 so the bag can more easily collect medical waste to be weighed and discarded as described below. The enclosure 110 is preferably formed of corrugated plastic but may be formed of any materials that are substantially water-proof and rigid.

An embodiment of the enclosure 110 is shaped as an inverted, truncated pyramid and has a planar floor 114 and four raised walls 116, 118, 120, 122. The floor 114 may be square or rectangular and has opposed upper and lower surfaces. In one embodiment, the floor 114 is 8-16" wide and 8-16" long. The walls 116-122 extend upwardly and angle outwardly from the floor and in one embodiment, are approximately 2-6" tall and angled outwardly approximately 10-30" with respect to a vertical axis. The upper rims of the walls together define the opening in the top of the enclosure. Non-skid rubber feet may be attached to the lower surface of the floor, so the enclosure doesn't slide on a weigh scale or other surface.

Figure 14:
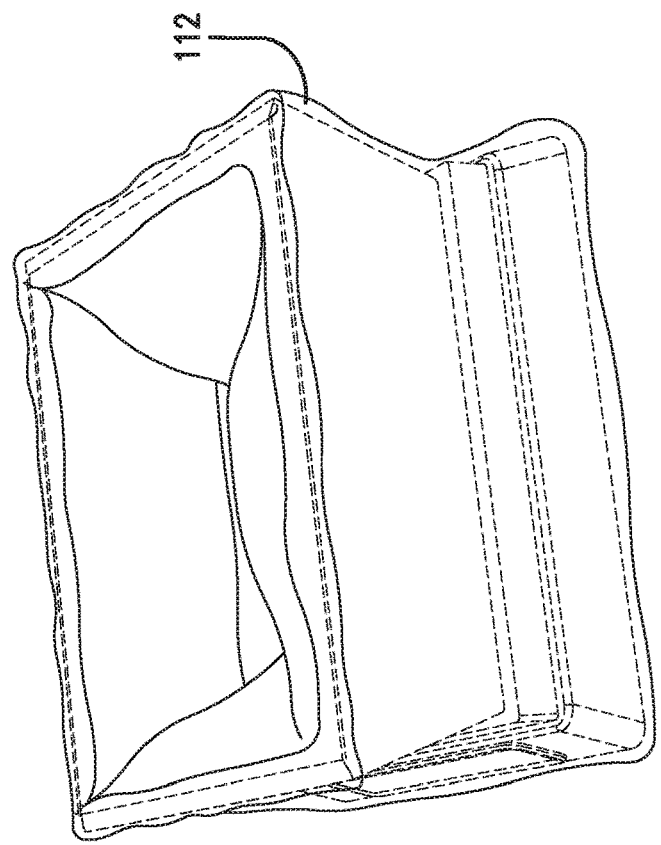
FIG. 14 is a perspective view of the disposable container of FIG. 12 showing its bag pulled over and covering the weigh scale.
Figure 16:
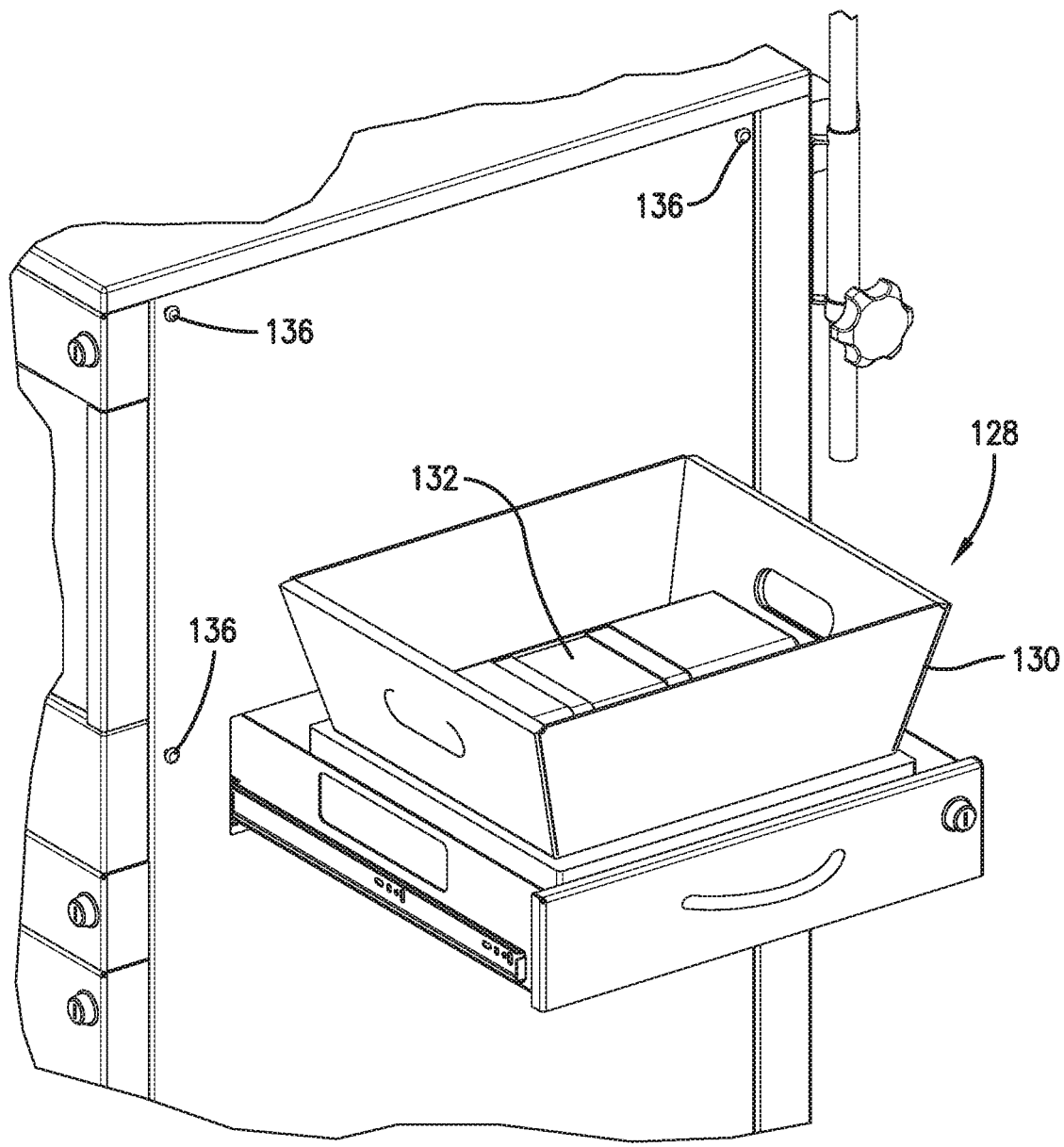
FIG. 16 is a perspective view of a disposable container constructed in accordance with yet another embodiment of the invention and shown supported on a weigh scale which is positioned in a scale drawer of the cart.

The hazardous waste bag 112 is provided for collecting, sealing, and disposing hazardous waste such as blood-soaked pads and needles. In one embodiment, the bag 112 is initially folded against the floor of the rigid enclosure 110 as shown in FIG. 12 and subsequently pulled out of the enclosure and over the scale to protect the scale from medical waste as shown in FIGS. 13 and 14.

An embodiment of the bag 112 comprises a closed lower end and an open upper end. The closed lower end is attached to the floor 114 of the rigid enclosure 110 with adhesives, staples, rivets, or other fasteners. The bag 112 is preferably formed of polyethylene but may be formed of any materials that are substantially water-proof and flexible. The bag may be of any size, and in one embodiment, holds a fluid volume of 1-20 gallons.

As best shown in FIG. 12, the entire container 108 may be placed on a scale 124 with the bag 112 initially folded against the floor 114 of the rigid enclosure 110. The bag 112 may then be pulled upwardly out of the enclosure 110 and pulled down over the sides of the enclosure and the scale as shown in FIGS. 13 and 14. The bag 112 thus covers the scale 124 and protects it from medical waste as it's placed in the bag. The bag may have a transparent portion that aligns with the display of the scale, so the display may be read through the bag.

Figure 15:
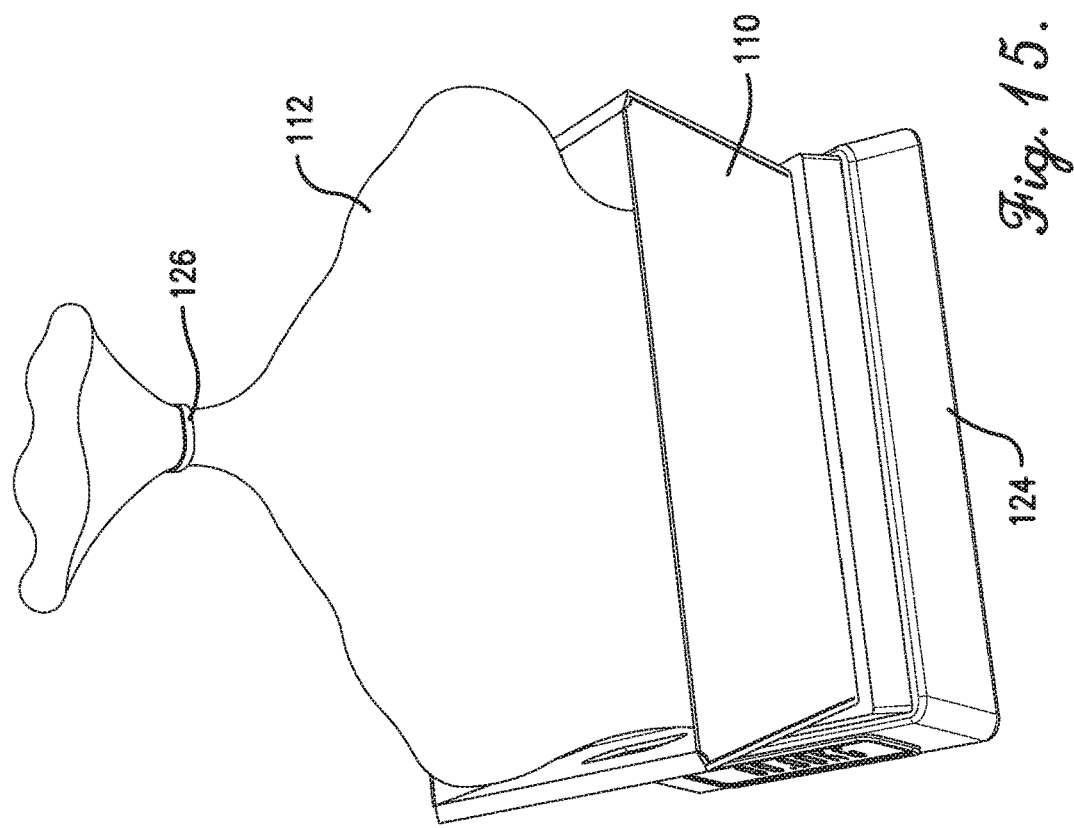
FIG. 15 is a perspective view of the disposable container of FIG. 12 showing its bag sealed for disposal.

During or after a medical procedure, the weight of the entire container 108 and its contents may be noted to estimate patient blood loss during the medical procedure. Specifically, the unfilled weight of the container 108 itself and the dry weight of any pads, sponges, etc. placed in the container are subtracted from the filled weight of the container to estimate the weight of blood soaked in the pads, sponges, etc. At the completion of the medical procedure, the upper end of the bag may be pulled up over the enclosure and closed to seal the medical waste in the bag as shown in FIG. 15. The entire container and its contents may then be discarded.

The bag may further comprise a closure mechanism 126 for sealing its upper end to contain the medical waste in the bag for safe disposal. The closure mechanism 126 may be interlocking grooves and ridges formed in the upper end of the bag that may be pressed together to close and seal the bag, a drawstring, tape, adhesives, or anything else that can close and seal the bag.

A disposable container 128 constructed in accordance with another embodiment of the invention is shown in FIGS. 16-19. This embodiment of the disposable container 128 also includes an open-topped enclosure 130 and a disposable bag 132 supported within and attached to the enclosure. The enclosure 130 is substantially identical to the enclosure 110 described above in connection with FIGS. 12-15, and therefore will not be described in detail again.

Figure 17:
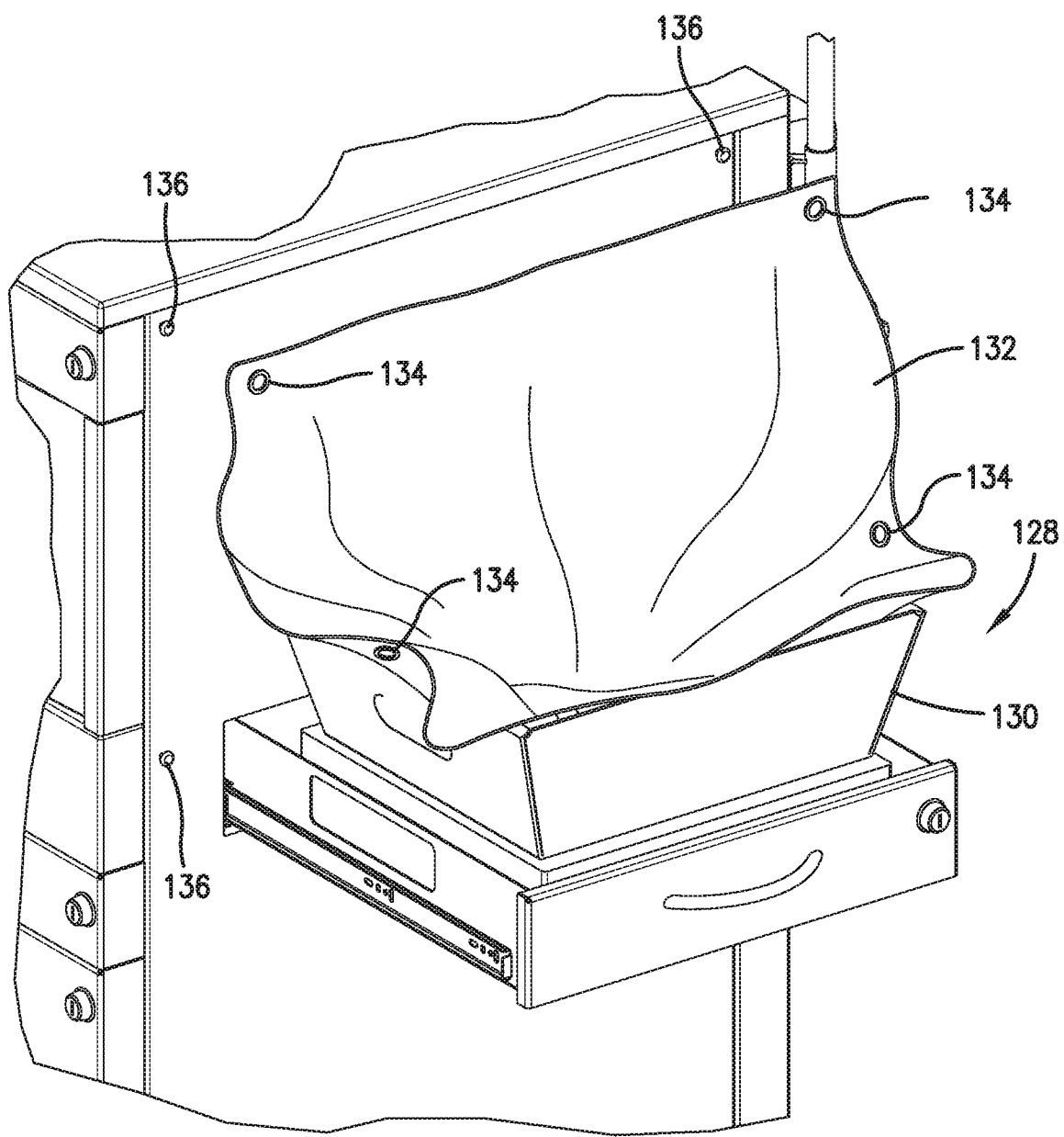
FIG. 17 is a perspective view of the disposable container of FIG. 16 showing its bag being raised out of its enclosure and attached to a wall of the cart.
Figure 18:
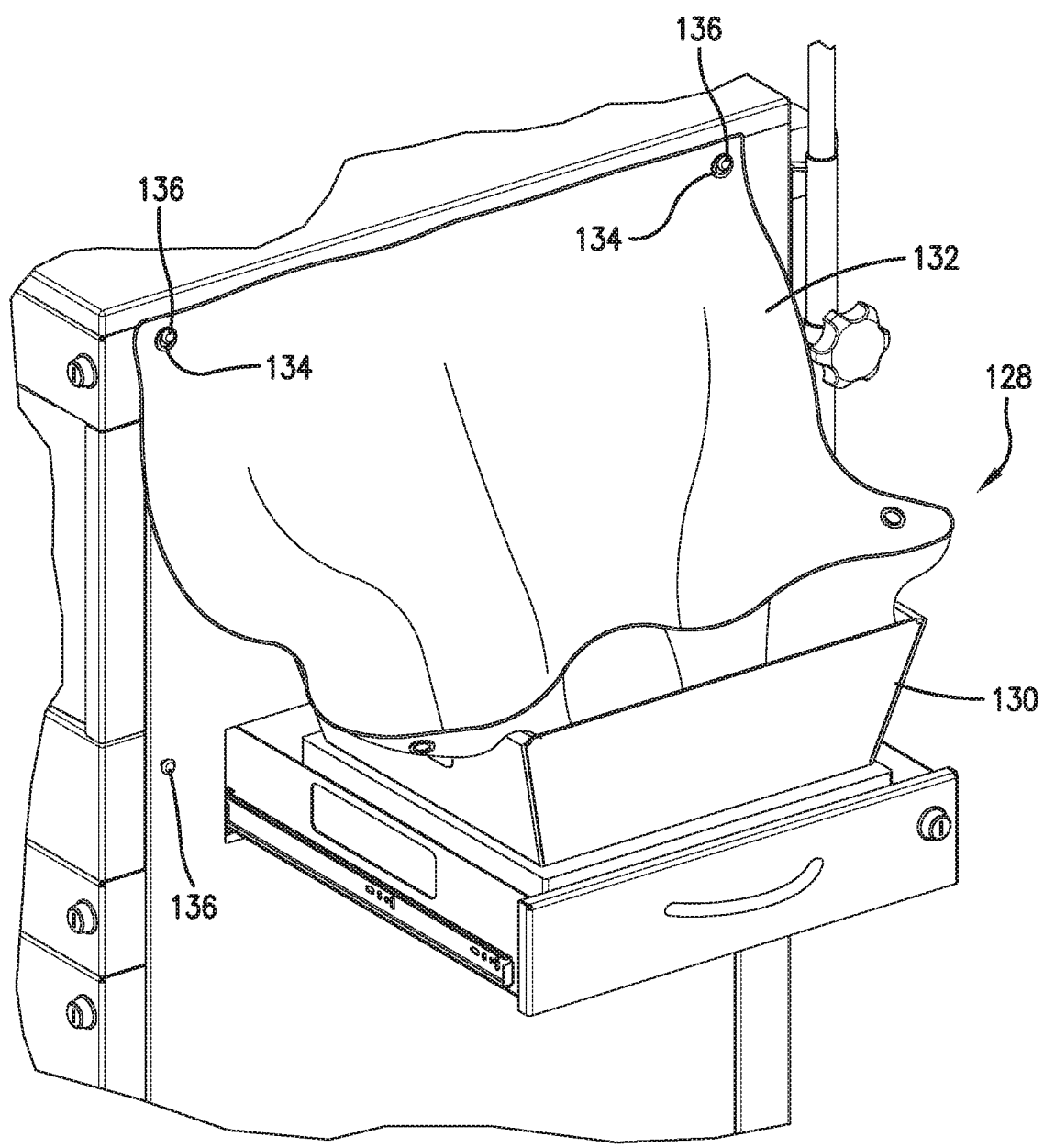
FIG. 18 is a continuation of FIG. 17 showing the bag fully being pulled over the weigh scale.
Figure 19:
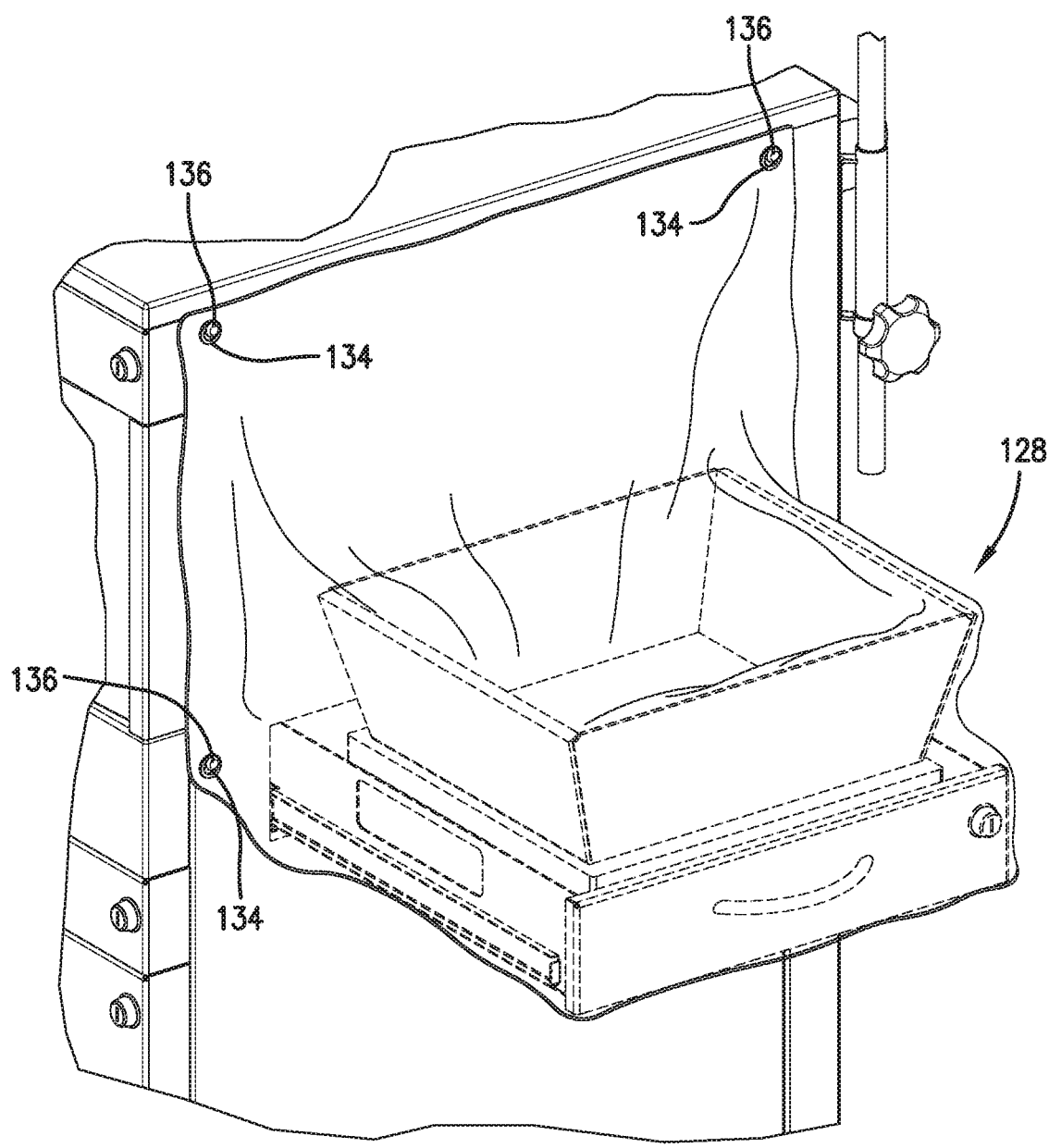
FIG. 19 is a continuation of FIG. 18 showing the bag fully attached to the wall of the cart and pulled over and covering the weigh scale.

The bag 132 is similar to the bag 112 described above but further comprises attachment mechanism for attaching its upper end to the mobile cart or other object on which the weigh scale is supported. In one embodiment, the attachment mechanism comprises grommets 134 for connecting to hooks or other projections 136 on the mobile cart or other object on which the weigh scale is supported as best shown in FIG. 17.

In use, the upper end of the bag 132 may be pulled out of the enclosure 130, and the grommets 134 may be attached to the projections 136 so the bag covers and shields the cart or other object from medical waste as it is placed in the bag.

The bag 132 may also be pulled down over the sides of the enclosure 130 and the scale to protect the scale from the medical waste. Medical waste may then be placed in the bag during or after a medical procedure. The weight of the container and its contents may be noted during or after a medical procedure, and then the bag may be closed to seal the medical waste in the bag so the entire container and its contents may be safely discarded.

In the above-described embodiments, the enclosures 110, 130 and bags 112, 132 are formed separately and attached. In other embodiments, the enclosures and bags may be integrally formed of the same material, with the enclosures being formed with thicker walls so they are more rigid to firmly rest on weigh scales and support the thinner, more flexible bags.

Although the inventions have been described with reference to the embodiments illustrated in the attached drawing figures, it is noted that equivalents may be employed and substitutions made herein without departing from the scope of the inventions as recited in the claims.

Having thus described various embodiments of the inventions, what is claimed as new and desired to be protected by Letters Patent includes the following:

The invention claimed is:
1. A medical cart comprising:
a frame;
a plurality of wheels attached to the frame;
a plurality of drawers slidably engaged to the frame;
a weigh scale positioned in one of the plurality of drawers and having a display; and
disposable container for collecting, weighing, and disposing medical waste from a medical procedure, the disposable container comprising:
an open-topped enclosure comprising
a rigid planar floor positioned on the weigh scale,
a number of raised walls with lower edges attached to the floor, and
upper rims that define an open-top; and
a flexible, open-topped bag supported within and attached to the enclosure for collecting medical waste to be weighed by the weigh scale, the bag including
a transparent portion that is aligned with the display of the weigh scale so that the display may be read through the transparent portion when the bag is pulled down over the scale,
a closed end attached to the floor of the enclosure,
an upper end which may be raised above the enclosure and attached to the frame so the bag shields the medical cart from the medical waste as the medical waste is placed in the bag, and
an attachment mechanism for attaching the upper end to the frame.

2. The medical cart as set forth in claim 1, the bag further comprising a closure mechanism for closing the upper end so as to contain the medical waste in the bag for safe disposal.

3. The medical cart as set forth in claim 1, wherein the enclosure is formed of rigid corrugated plastic.

4. The medical cart as set forth in claim 1, wherein the bag is formed of flexible polyethylene.

5. The medical cart as set forth in claim 1, wherein the bag is attached to the enclosure with a fastener comprising at least one of an adhesive, a staple, or a rivet.

6. The medical cart as set forth in claim 1, wherein the bag is integrally formed with the enclosure.

7. The medical cart as set forth in claim 1, wherein the enclosure is cylindrical in shape.

8. The medical cart as set forth in claim 1, wherein the enclosure is in the shape of an inverted, truncated pyramid.

9. A medical cart comprising:
a frame;
a plurality of wheels attached to the frame;
a plurality of drawers slidably engaged to the frame;
a scale positioned in one of the plurality of drawers and having a display;
a disposable container for collecting, weighing, and disposing medical waste from a medical procedure, the disposable container comprising
a rigid enclosure positioned on the scale, the enclosure comprising
a rectangular planar floor having opposed upper and lower surfaces, and
four raised walls with lower edges attached to the floor and upper edges that together define an open-top; and
a flexible bag for collecting medical waste to be weighed by the scale, the bag comprising
a transparent portion that is aligned with the display of the scale when the bag is pulled down over the scale so that the display may be read through the transparent portion,
a bottom end attached to the upper edges of the walls of the enclosure,
an upper end that defines an open-top, and
an attachment mechanism for attaching the upper end to the frame so the bag shields the medical cart from the medical waste as the medical waste is placed in the bag.

10. The medical cart as set forth in claim 9, the attachment mechanism comprising grommets in the upper end of the bag for connecting to hooks on the frame.

11. The medical cart as set forth in claim 9, the bag further comprising a closure mechanism for closing the upper end of the bag so as to contain the medical waste in the bag for safe disposal.

12. The medical cart as set forth in claim 11, the closure mechanism comprising an interlocking groove and ridge formed in the upper end of the bag.

13. A medical cart comprising:
a frame;
a plurality of wheels attached to the frame;
a plurality of drawers slidably engaged to the frame;
a scale positioned in one of the plurality of drawers and having a display;
a disposable container for collecting, weighing, and disposing medical waste from a medical procedure, the disposable container comprising:
a rigid enclosure positioned on the scale, the enclosure comprising
a rectangular planar floor having opposed upper and lower surfaces,
non-skid feet on the lower surface of the floor, and
four raised walls extending upwardly and angled outwardly from the floor with lower edges attached to the floor and upper edges that together define an open-top so that the enclosure forms an inverted, truncated pyramid shape; and
a flexible bag supported by and integrally connected to the enclosure for collecting medical waste to be weighed by the weigh scale, the bag being formed of flexible polyethylene and comprising a bottom end attached to the upper edges of the walls of the enclosure, an upper end that defines an open-top, an attachment mechanism attached to the frame so the bag shields the frame and the plurality of drawers from the medical waste as it is placed in the bag, a closure mechanism for closing the open-top of the bag so as to contain the medical waste in the bag for safe disposal; and a transparent portion that may be aligned with the display of the scale so that the display may be read through the transparent portion;

wherein the enclosure is formed with walls thicker than the flexible bag so that it is more rigid to firmly rest on the scale and support the flexible bag.

* * * * *